(12) United States Patent
Lee

(10) Patent No.: US 9,060,734 B2
(45) Date of Patent: Jun. 23, 2015

(54) FIXED FOCUS TRANSDUCER ARRAY AND ULTRASONIC WAVE TRANSCEIVING APPARATUS USING THE SAME

(75) Inventor: Seung Seoup Lee, Gyunggi-do (KR)

(73) Assignee: SAMSUNG ELECTRO-MECHANICS CO., LTD., Suwon-Si, Gyeonggi-Do (KR)

( * ) Notice: Subject to any disclaimer, the term of this patent is extended or adjusted under 35 U.S.C. 154(b) by 513 days.

(21) Appl. No.: 13/360,458

(22) Filed: Jan. 27, 2012

(65) Prior Publication Data

US 2013/0131515 A1    May 23, 2013

(30) Foreign Application Priority Data

Nov. 22, 2011    (KR) .................. 10-2011-0122241

(51) Int. Cl.
     *A61B 8/00*      (2006.01)
(52) U.S. Cl.
     CPC ............. *A61B 8/4477* (2013.01); *A61B 8/4483* (2013.01); *A61B 8/4494* (2013.01); *A61B 8/44* (2013.01)
(58) Field of Classification Search
     USPC ........................................................ 600/447
     See application file for complete search history.

(56) References Cited

U.S. PATENT DOCUMENTS

| 5,166,907 | A | * | 11/1992 | Newnham et al. ............ 367/157 |
| 2007/0016049 | A1 | | 1/2007 | Kye | |
| 2008/0045838 | A1 | * | 2/2008 | Hyuga ........................ 600/463 |

FOREIGN PATENT DOCUMENTS

| JP | 2008-005996 A | 1/2008 |
| KR | 10-0847797 B1 | 1/2007 |
| KR | 10-2011-0022440 A | 3/2011 |

OTHER PUBLICATIONS

Piezoelectric Transducer Materials by H. Jaffe Proceedings of the IEEE vol. 53, No. 10 Oct. 1965.*
Office Action issued in related Korean Application No. 10-2011-0122241 dated Dec. 5, 2012.

* cited by examiner

*Primary Examiner* — Long V Le
*Assistant Examiner* — Michael Kellogg
(74) *Attorney, Agent, or Firm* — McDermott Will & Emery LLP

(57) ABSTRACT

There are provided a fixed focus transducer array and an ultrasonic wave transceiving apparatus using the same. The fixed focus transducer array includes: a plurality of transducers, transducing electrical signals into ultrasonic signals to thereby focus the ultrasonic signals on a single focal point and transducing reflected ultrasonic signals from the single focal point into electrical signals to thereby output the electrical signals, wherein the plurality of transducers are disposed to be symmetrical to each other based on one transducer and simultaneously focus the ultrasonic signals on the single focal point at speeds according to the respective natural frequencies thereof. Therefore, a circuit area is reduced, whereby miniaturization may be implemented and a processing speed may be increased.

12 Claims, 5 Drawing Sheets

FIXED FOCUS TRANSDUCER ARRAY AND ULTRASONIC WAVE TRANSCEIVING APPARATUS USING THE SAME

CROSS-REFERENCE TO RELATED APPLICATIONS

This application claims the priority of Korean Patent Application No. 10-2011-0122241 filed on Nov. 22, 2011, in the Korean Intellectual Property Office, the disclosure of which is incorporated herein by reference.

BACKGROUND OF THE INVENTION

1. Field of the Invention

The present invention relates to a fixed focus transducer array used in an ultrasonic medical device and an ultrasonic wave transceiving apparatus using the same.

2. Description of the Related Art

Generally, an ultrasonic wave transceiving apparatus used in a medical device transmits an ultrasonic signal to an object to be inspected, receives an ultrasonic signal reflected and returned from a discontinuous surface of the object, transduces the received ultrasonic signal into an electrical signal, and then outputs the transduced electrical signal to a predetermined image apparatus, thereby allowing for the inspection of an internal state of the object.

More specifically, as shown in FIG. 1, ultrasonic signals may be obtained by applying transmission pulse signals to a transducer array 100. That is, transmission pulse signals are transduced into ultrasonic signals by respective transducers 110 included in the transducer array 100, and then transmitted to the object. In this situation, in order to raise the resolution of an ultrasonic image, a method of transmitting and focusing ultrasonic waves transmitted from the respective transducer 110 on a focal point along a scan line is used.

Therefore, in the case in which the transducers 110, provided in plural, are arranged in a linear array form, there is a need to control the transmission pulse signals transmitted to the respective transducer 110 in order to perform focusing on the focal point. That is, the ultrasonic signals transmitted from all of the transducers 110 are controlled to simultaneously arrive at a single focal point by allowing transmission pulse signals of transducers distant from the focal point to be first transferred, and delaying the transmission of pulse signals of transducers close to the focal point to arrive relatively late.

In addition, the arrival times of ultrasonic signals reflected from the object to thereby be incident to the transducers are different, according to positions of the respective transducers. The ultrasonic signals incident at the different arrival times, as described above, are transduced into electrical signals by respective transducing elements. In this case, in order to focus electrical signals output from respective transducing elements, compensation needs to be performed by delaying each of times, by a period corresponding to differences in arrival times.

Therefore, according to the related art described above, a circuit for delaying the transmission pulse signal or a separate circuit for performing delay-compensation on the received signal needs to be added, which may cause an increase in a circuit area and a decrease in a processing speed thereof. The above-mentioned problem is intensified, particularly in the case of a small device such as a cellular phone in which a plurality of circuits may be integrated.

SUMMARY OF THE INVENTION

An aspect of the present invention provides a fixed focus transducer array capable being miniaturized by having a reduced circuit area and increasing a processing speed, and an ultrasonic wave transceiving apparatus using the same.

According to an aspect of the present invention, there is provided a fixed focus transducer array including: a plurality of transducers, transducing electrical signals into ultrasonic signals to thereby focus the ultrasonic signals on a single focal point and transducing reflected ultrasonic signals from the single focal point into electrical signals to thereby output the electrical signals, wherein the plurality of transducers are disposed to be symmetrical to each other based on one transducer and simultaneously focus the ultrasonic signals on the single focal point at speeds according to the respective natural frequencies thereof.

The plurality of transducers may include piezoelectric elements having the same density and height, and the respective natural frequencies of the plurality of transducers may be determined according to sizes of cross sections of the plurality of transducers.

The plurality of transducers may have cross sections with sizes gradually reduced from a center region of the transducer array toward a surrounding region thereof.

The plurality of transducers may have a circular cross section or a rectangular cross section.

The plurality of transducers may include piezoelectric elements having the same height and cross-sectional area, and the respective natural frequencies of the plurality of transducers may be determined according to density magnitudes of the plurality of transducers. The plurality of transducers may have density magnitudes gradually reduced from a center region of the transducer array toward a surrounding region thereof.

According to another aspect of the present invention, there is provided an ultrasonic wave transceiving apparatus including: a transmission beam forming unit forming electrical signals for ultrasonic signals; a transducer array including a plurality of transducers, transducing the electrical signals formed by the transmission beam forming unit into the ultrasonic signals to thereby focus the ultrasonic signals on a single focal point and transducing reflected ultrasonic signals from the single focal point into electrical signals to thereby output the electrical signals; and a reception beam forming unit combining the electrical signals output from the transducer array to thereby output an combined electrical signal, wherein the plurality of transducers are disposed to be symmetrical to each other based on one transducer and simultaneously focus the ultrasonic signals on the single focal point at speeds according to the respective natural frequencies thereof.

The plurality of transducers may include piezoelectric elements having the same density and height, and the respective natural frequencies of the plurality of transducers may be determined according to sizes of cross sections of the plurality of transducers.

The plurality of transducers may have cross sections with sizes gradually reduced from a center region of the transducer array toward a surrounding region thereof. The plurality of transducers may have a circular cross section or a rectangular cross section.

The plurality of transducers may include piezoelectric elements having the same height and cross-sectional area, and the respective natural frequencies of the plurality of transducers may be determined according to density magnitudes of the plurality of transducers.

The plurality of transducers may have density magnitudes gradually reduced from a center region of the transducer array toward a surrounding region thereof.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE INVENTION

Figure 1:
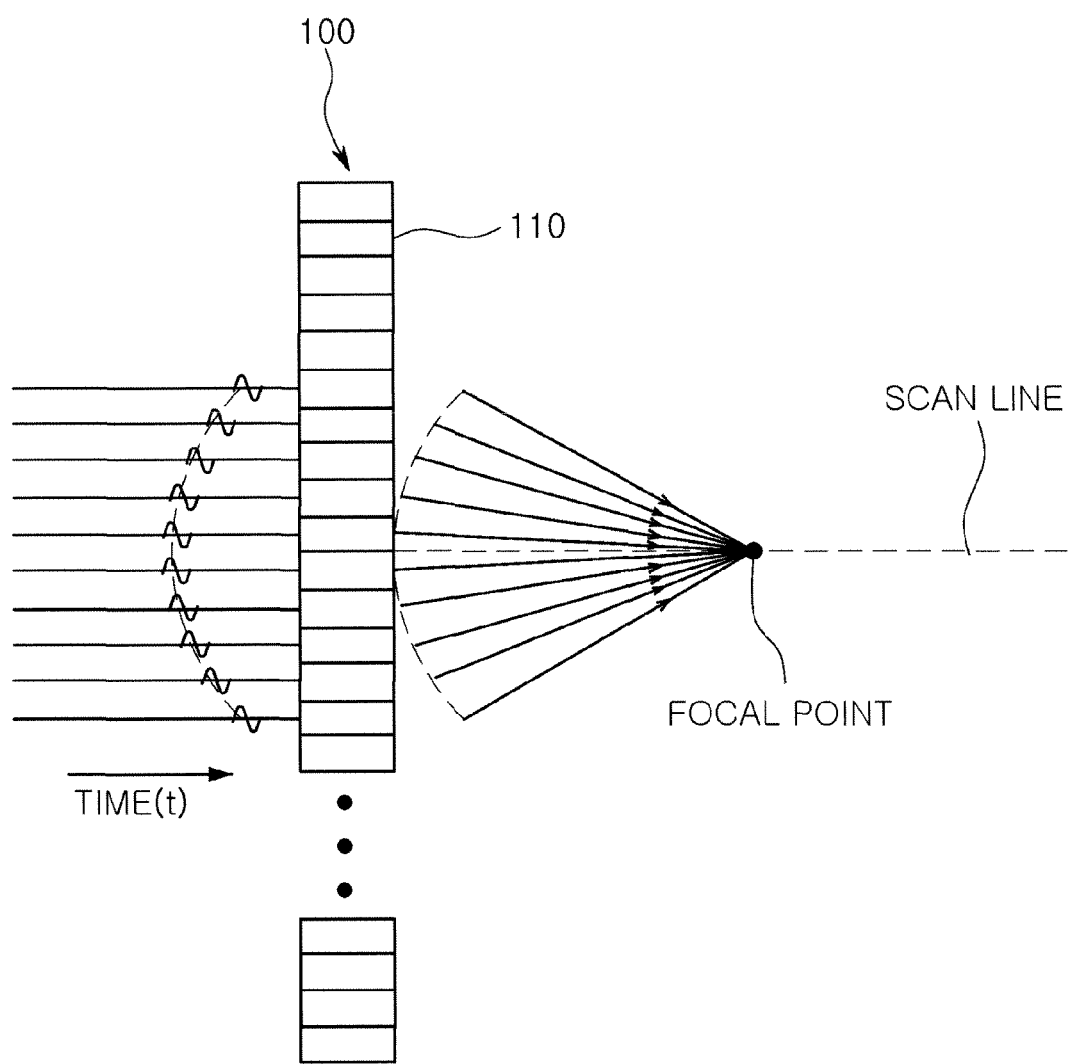
FIG. 1 is a view describing an ultrasonic wave transceiving method according to the related art.

Embodiments of the present invention will now be described in detail with reference to the accompanying drawings. However, the exemplary embodiments of the present invention may be modified in many different forms and the scope of the invention should not be limited to the embodiments set forth herein. In the drawings, the shapes and dimensions may be exaggerated for clarity, and the same reference numerals will be used throughout to designate the same or like components.

Figure 2:
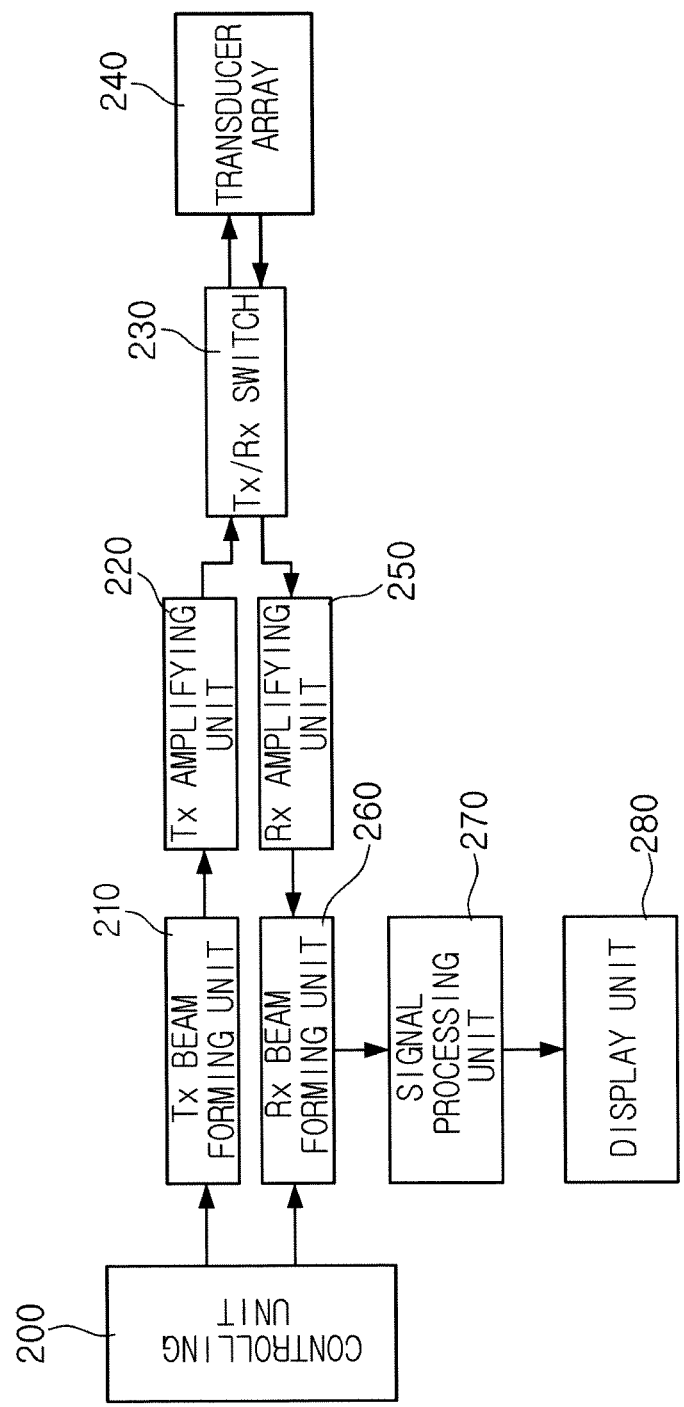
FIG. 2 is a configuration diagram of an ultrasonic wave transceiving apparatus according to an embodiment of the present invention.
Figure 3:
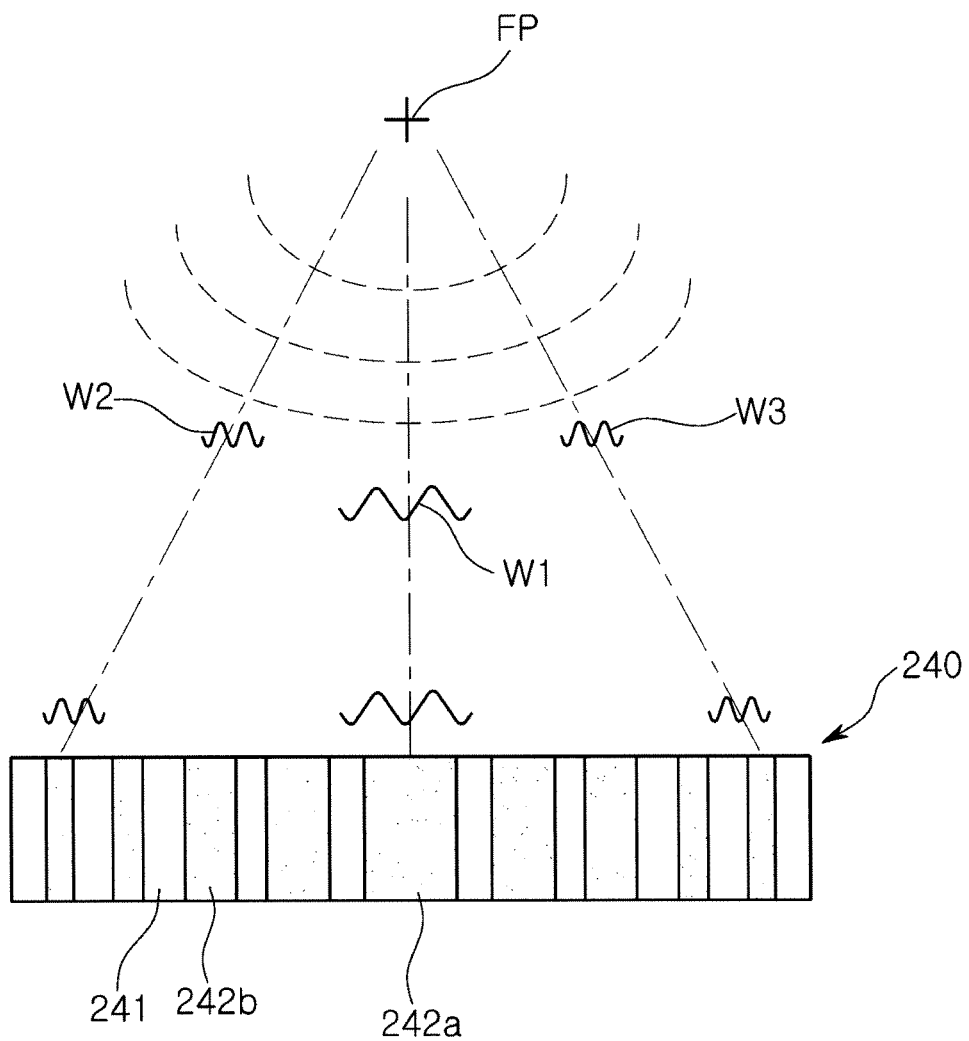
FIG. 3 is a view describing an ultrasonic wave transceiving method according to the embodiment of the present invention.

FIG. 2 is a configuration diagram of an ultrasonic wave transceiving apparatus according to an embodiment of the present invention; and FIG. 3 is a view describing an ultrasonic wave transceiving method according to the embodiment of the present invention. FIGS. 4A through 4D are views showing various forms of a transducer array according to the embodiment of the present invention.

The ultrasonic wave transceiving apparatus according to the embodiment of the present invention may include a transmission beam forming unit 210 forming electrical signals for ultrasonic signals, a transducer array 240 including a plurality of transducers 242a and 242b transducing the electrical signals formed by the transmission beam forming unit 210 into ultrasonic signals to thereby focus the ultrasonic signals on a single focal point (FP) and transducing reflected ultrasonic signals from the single focal point (FP) into electrical signals to thereby output the electrical signals, and a reception beam forming unit 260 combining the electrical signals output from the transducer array 240 to thereby output the combined electrical signal. Meanwhile, the plurality of transducers 242a and 242b may be disposed to be symmetrical to each other based on one transducer 242a and simultaneously focus the ultrasonic signals on the single focal point (FP) at speeds according to the respective natural frequencies thereof.

Hereinafter, the ultrasonic wave transceiving apparatus according to the embodiment of the present invention will be described in detail with reference to FIGS. 2 through 4D.

First, referring to FIGS. 2 and 3, a controlling unit 200 may control the transmission beam forming unit 210 to thereby form the electrical signals for ultrasonic signals, for example, transmission pulse signals, and may control the transmission beam forming unit 210 to thereby combine the electrical signals output from the transducer array 240 and output the combined electrical signal.

The transmission beam forming unit (a Tx beam forming unit) 210 may form the electrical signals for ultrasonic signals, for example, the transmission pulse signals according to the control of the controlling unit 200. The formed transmission pulse signals may be transmitted to a Tx amplifying unit 220.

The Tx amplifying unit 220 may amplify the transmission pulse signals formed by the transmission beam forming unit 210 by an appropriate gain and then transfer the amplified transmission pulse signals to the transducer array 240 through a Tx/Rx switch 230.

The transducer array 240 may include the plurality of transducers 242a and 242b. The respective transducers 242a and 242b may transduce the electrical signals formed by the transmission beam forming unit 210 into ultrasonic signals to thereby focus the ultrasonic signals on the single focal point (FP) and transduce reflected ultrasonic signals from the single focal point (FP) into electrical signals to thereby output the electrical signals.

The transducer array 240 may be in the form of a 1-3 composite array in which piezoelectric elements such as the transducers 242a and 242b are buried in polymers 241, and the plurality of transducers 242a and 242b may be disposed to be symmetrical to each other based on one transducer 242a and simultaneously focus the ultrasonic signals on the single focal point (FP) at speeds according to respective natural frequencies thereof.

Generally, a natural frequency of a structure including the transducers 242a and 242b may be in inverse proportional to mass thereof and be in proportion to rigidity thereof. Therefore, in the case in which the transducers 242a and 242b have the same cross-sectional area (width) and density (it is assumed that they have the same rigidity), the natural frequency of the transducers 242a and 242b having a small height (length) increases, such that ultrasonic waves generated from the transducers 242a and 242b are generated at a frequency equal to the natural frequency of the transducers 242a and 242b. In addition, since a speed of the ultrasonic wave is in proportion to the frequency thereof, when the natural frequency (frequency) of the ultrasonic wave is high, a propagation speed is rapid, and when the natural frequency of the ultrasonic wave is low, a propagation speed is slow.

Similarly, as shown in FIG. 3, when it is assumed that the respective transducers 242a and 242b are piezoelectric elements having the same density and height, the transducers 242a and 242b may be designed to have different natural frequencies by having different-sized cross sections.

Figure 4A:
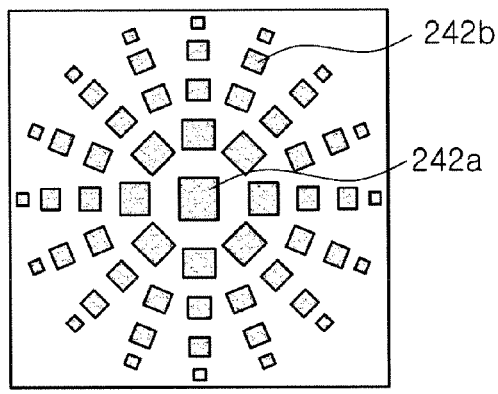
FIGS. 4A through 4D are views showing various forms of a transducer array according to the embodiment of the present invention.
Figure 4B:
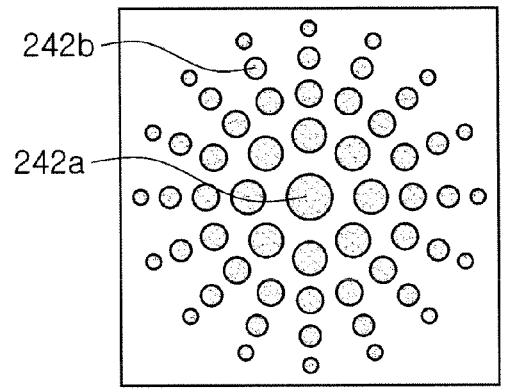
Figure 4C:
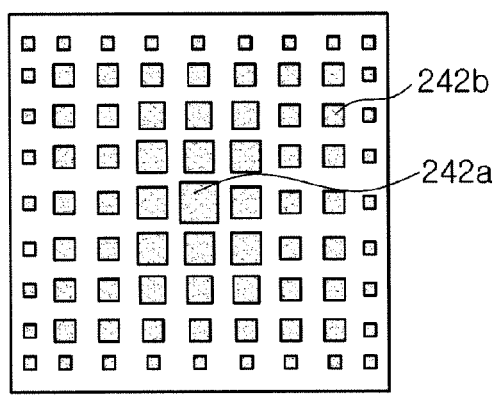
Figure 4D:
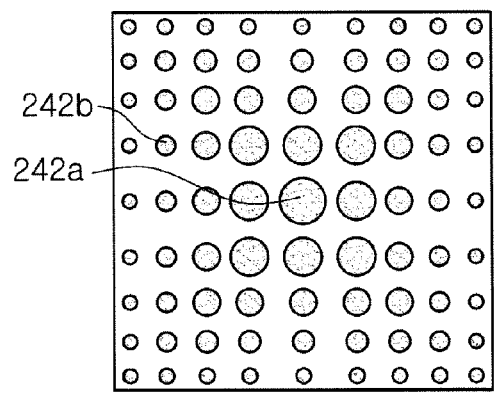

Therefore, in this case, when the transducer 242a disposed in the center of the transducer array 240 is designed to have a cross section with the largest size and the remaining transducers 242b are designed to have cross sections with sizes gradually reduced from the center of the transducer array 240 toward the surroundings thereof, the transducer 242a disposed in the center of the transducer array 240 has a highest ultrasonic wave speed W1 and the transducers disposed in the outermost portions of the transducer array 240 have lowest ultrasonic wave speeds W2 and W3. Through the principle, the ultrasonic waves generated from the respective transducers 242a and 242b may be focused on the single focal point (FP). The cross section of the transducers 242a and 242b may have various shapes as shown in FIGS. 4A through 4D. More specifically, according to the embodiment of the present invention, the cross sections of the transducers 242a and 242b may have a rectangular shape as shown in FIGS. 4A and 4C. According to another embodiment of the present invention, the cross sections of the transducers 242a and 242b may have a circular shape as shown in FIGS. 4B and 4D. The shape of the cross sections of the transducers 242a and 242b is only an example and may be variously changed by those skilled in the art as needed.

According to another embodiment of the present invention, when it is assumed that the plurality of transducers 242a and 242b are the piezoelectric elements having the same height and cross-sectional area, the respective natural frequencies of the plurality of transducers 242a and 242b may be determined according to density magnitudes of the transducers 242a and 242b. That is, in this case, when the transducer 242a disposed in the center of the transducer array 240 is designed to have a highest density magnitude and the remaining transducers 242b are designed to have density magnitudes gradually reduced from the center of the transducer array 240 toward the surroundings thereof, the transducer 242a disposed in the center of the transducer array 240 has the highest ultrasonic wave speed W1 and the transducers disposed in the outermost portions of the transducer array 240 have the lowest ultrasonic wave speeds W2 and W3. In this case, the cross sections of the transducers 242a and 242b may have a circular shape or a rectangular shape as shown in FIGS. 4A through 4D; however, the cross sections of the transducers 242a and 242b need to have the same size.

As described above, in order to focus the ultrasonic signals transduced by the respective transducers 242a and 242b on the single focal point (FP), a separate external delay circuit is not required. Instead, the respective transducers 242a and 242b are designed to have different natural frequencies, whereby the ultrasonic signals generated from the respective transducers 242a and 242b may be focused on the single focal point (FP) at the same time.

In addition, a Rx amplifying unit 250 may amplify the electrical signals transmitted from the transducer array 240 by an appropriate gain and then transmit the amplified electrical signals to the reception beam forming unit 260.

The reception beam forming unit (a Rx beam forming unit) 260 may combine the electrical signals transmitted from the transducer array 240 through a Tx/Rx switch 230 to thereby output the combined electrical signal. The combined electrical signal may be transmitted to a signal processing unit 270.

The signal processing unit 270 may perform appropriate signal processing on the electrical signal transmitted from the reception beam forming unit 260 and then transmit a signal processing result to a display unit 280. According to the embodiment of the present invention, the signal processing unit 270 may determine whether a blood flow is present in the focal point (FP), based on a change in a frequency caused by a Doppler effect of the electrical signal transferred from the reception beam forming unit 260. The above-mentioned technology may be applied to a living body fingerprint recognition field, or the like.

Finally, the display unit 280 may display the signal processing result transmitted from the signal processing unit 270 in a two-dimension or a three-dimension.

As described above, according to the embodiment of the present invention, the plurality of transducers included in the transducer array are designed on the basis of the respective natural frequencies thereof so that the ultrasonic signals may be simultaneously focused on the single focal point, whereby a circuit area may be reduced to thereby allow for miniaturization and a increased processing speed.

Figure 5:
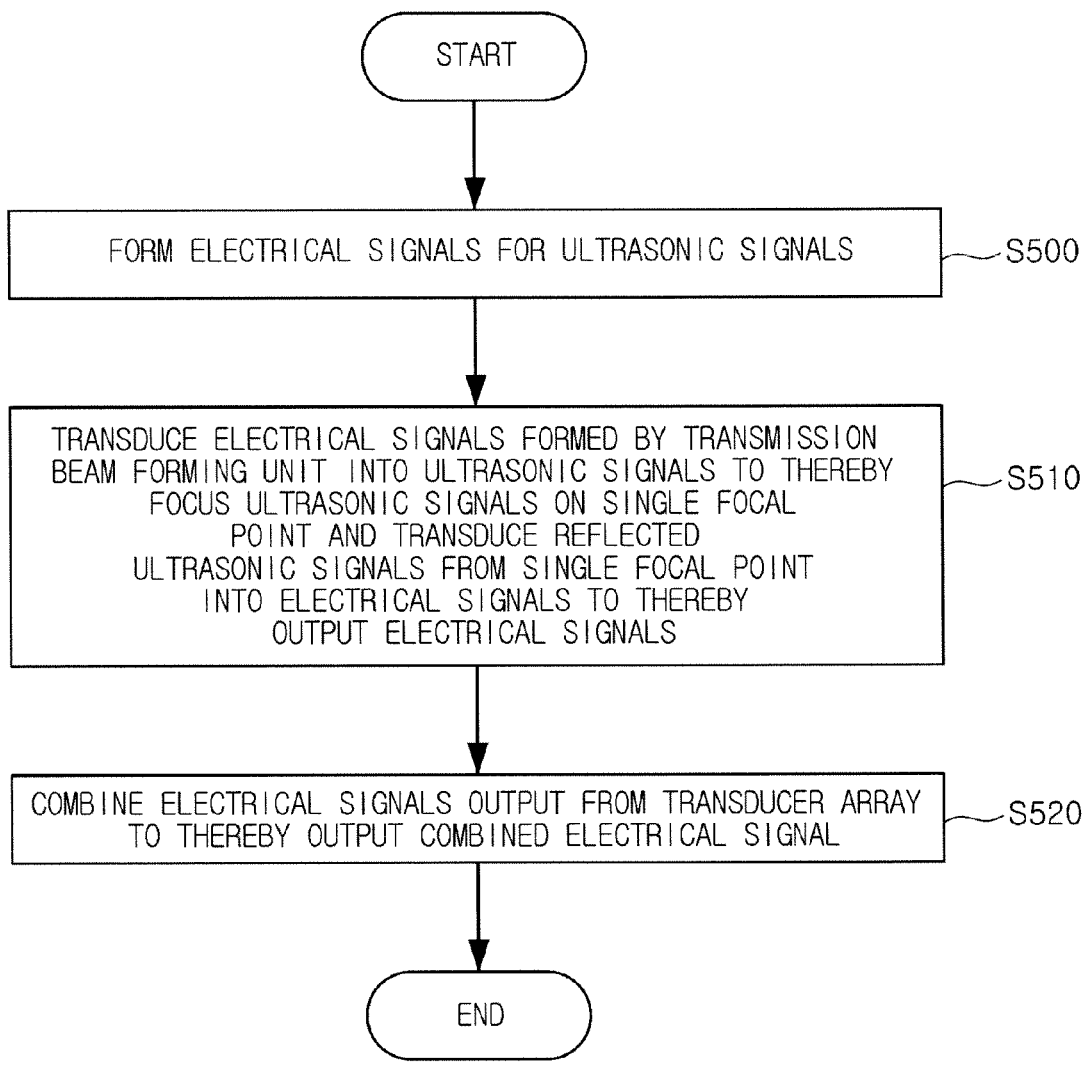
FIG. 5 is a flow chart describing an ultrasonic wave transceiving method according to the embodiment of the present invention.

Finally, FIG. 5 is a flow chart describing an ultrasonic wave transceiving method according to the embodiment of the present invention. For simplification of explanation, a description of contents overlapped with contents described with reference to FIGS. 2 through 4D will be omitted.

Referring to FIGS. 2 and 5, first, the transmission beam forming unit 210 may form the electrical signals for ultrasonic signals, for example, the transmission pulse signals according to the control of the controlling unit 200 (S500). The formed transmission pulse signals may be amplified by an appropriate gain by the Tx amplifying unit 220 and be then transmitted to the transducer array 240 through the Tx/Rx switch 230.

Next, the respective transducers 242a and 242b of the transducer array 240 may transduce the electrical signals formed by the transmission beam forming unit 210 into the ultrasonic signals to thereby focus the ultrasonic signals on the single focal point (FP) and transduce reflected ultrasonic signals from the single focal point (FP) into electrical signals to thereby output the electrical signals (S510).

The transducer array 240 may be in the form of a 1-3 composite array in which piezoelectric elements such as the transducers 242a and 242b are buried in the polymers 241, and the plurality of transducers 242a and 242b may be disposed to be symmetrical to each other based on one transducer 242a and simultaneously focus the ultrasonic signals on the single focal point (FP) at speeds according to the respective natural frequencies.

According to the embodiment of the present invention, when it is assumed that the plurality of transducers 22a and 242b are piezoelectric elements having the same density and height, the respective natural frequencies of the plurality of transducers 242a and 242b may be determined according to the sizes of the cross sections of the transducers 242a and 242b, and the transducers 242a and 242b are designed to have the cross sections with sizes gradually reduced from the center of the transducer array 240 toward the surroundings thereof, whereby the ultrasonic signals may be simultaneously focused on the single focal point (FP). Here, the cross-sections of the plurality of transducers 242a and 242b may have a circular shape, a rectangular shape, or the like, as shown in FIGS. 4A through 4D.

According to another embodiment of the present invention, when it is assumed that the plurality of transducers 22a and 242b are the piezoelectric elements having the same height and cross-sectional area, the respective natural frequencies of the plurality of transducers 242a and 242b may be determined according to the density magnitudes of the transducers 242a and 242b, and the transducers 242a and 242b are designed to have the density magnitudes gradually reduced from the center of the transducer array 240 toward the surroundings thereof, whereby the ultrasonic signals may be simultaneously focused on the single focal point (FP). In this case, the cross sections of the transducers may have a circular shape or a rectangular shape as shown in FIGS. 4A through 4D, but need to have the same size.

Finally, the reception beam forming unit 260 may combine the electrical signals output from the transducer array 240 to thereby output the combined electrical signal (S520). The combined electrical signal may be transmitted to the signal processing unit 270. Then, the signal processing unit 270 may perform appropriate signal processing on the combined electrical signal transmitted from the reception beam forming unit (the Rx beam forming unit) 260 and then transmit a signal processing result to the display unit 280, thereby allowing the display unit 280 to display the signal processing result in a two-dimension or a three-dimension. According to the embodiment of the present invention, the signal processing unit 270 may determine whether a blood flow is present in the focal point (FP) based on a change in a frequency caused by a Doppler effect of the electrical signal transmitted from the reception beam forming unit 260. The above-mentioned technology may be applied to a living body fingerprint recognition field, or the like.

As set forth, according to the embodiment of the present invention, the plurality of transducers included in the transducer array are designed on the basis of the respective natural frequencies thereof so that the ultrasonic signals may be simultaneously focused on the single focal point, whereby a circuit area may be reduced to thereby allow for miniaturization and a increased processing speed.

While the present invention has been shown and described in connection with the embodiments, it will be apparent to those skilled in the art that modifications and variations can be made without departing from the spirit and scope of the invention as defined by the appended claims.

What is claimed is:

1. A fixed focus transducer array, comprising:
    a central piezoelectric transducer; and
    a plurality of peripheral piezoelectric transducers symmetrically disposed around the central piezoelectric transducer;
    wherein the central piezoelectric transducer and the plurality of peripheral piezoelectric transducers focus ultrasonic signals onto a single focal point with each ultrasonic signal propagating at a speed determined in accordance with the natural frequency of the respective piezoelectric transducer such that the ultrasonic signals transduced by the central piezoelectric transducer and the plurality of peripheral piezoelectric transducers simultaneously arrive at the single focal point, and
    wherein the speed of the ultrasonic signal transduced by the central piezoelectric transducer is different from the speeds of the ultrasonic signals transduced by the plurality of peripheral piezoelectric transducers.

2. The fixed focus transducer array of claim 1, wherein the plurality of transducers include piezoelectric elements having the same density and height, and
    the respective natural frequencies of the plurality of transducers are determined according to sizes of cross sections of the plurality of transducers.

3. The fixed focus transducer array of claim 2, wherein the plurality of transducers have cross sections with sizes gradually reduced from a center region of the transducer array toward a surrounding region thereof.

4. The fixed focus transducer array of claim 1, wherein the plurality of transducers have a circular cross section or a rectangular cross section.

5. The fixed focus transducer array of claim 1, wherein the plurality of transducers include piezoelectric elements having the same height and cross-sectional area, and
    the respective natural frequencies of the plurality of transducers are determined according to density magnitudes of the plurality of transducers.

6. The fixed focus transducer array of claim 5, wherein the plurality of transducers have density magnitudes gradually reduced from a center region of the transducer array toward a surrounding region thereof.

7. An ultrasonic wave transceiving apparatus, comprising:
    a transmission beam forming unit forming electrical signals for ultrasonic signals;
    a transducer array including a central piezoelectric transducer and a plurality of peripheral piezoelectric transducers symmetrically disposed around the central piezoelectric transducer; and
    a reception beam forming unit combining the electrical signals output from the transducer array to thereby output an combined electrical signal;
    wherein the central piezoelectric transducer and the plurality of peripheral piezoelectric transducers focus ultrasonic signals onto a single focal point with each ultrasonic signal propagating at a speed determined in accordance with the natural frequency of the respective piezoelectric transducer such that the ultrasonic signals transduced by the central piezoelectric transducer and the plurality of peripheral piezoelectric transducers simultaneously arrive at the single focal point, and
    wherein the speed of the ultrasonic signal transduced by the central piezoelectric transducer is different from the speeds of the ultrasonic signals transduced by the plurality of peripheral piezoelectric transducers.

8. The ultrasonic wave transceiving apparatus of claim 7, wherein the plurality of transducers include piezoelectric elements having the same density and height, and
    the respective natural frequencies of the plurality of transducers are determined according to sizes of cross sections of the plurality of transducers.

9. The ultrasonic wave transceiving apparatus of claim 8, wherein the plurality of transducers have cross sections with sizes gradually reduced from a center region of the transducer array toward a surrounding region thereof.

10. The ultrasonic wave transceiving apparatus of claim 7, wherein the plurality of transducers have a circular cross section or a rectangular cross section.

11. The ultrasonic wave transceiving apparatus of claim 7, wherein the plurality of transducers include piezoelectric elements having the same height and cross-sectional area, and
    the respective natural frequencies of the plurality of transducers are determined according to density magnitudes of the plurality of transducers.

12. The ultrasonic wave transceiving apparatus of claim 11, wherein the plurality of transducers have density magnitudes gradually reduced from a center region of the transducer array toward a surrounding region thereof.

* * * * *